US008669294B2

(12) United States Patent
Lien et al.

(10) Patent No.: US 8,669,294 B2
(45) Date of Patent: Mar. 11, 2014

(54) SYNGAS PRODUCTION THROUGH THE USE OF MEMBRANE TECHNOLOGIES

(71) Applicant: EcoTechnol Pty Ltd., Perth (AU)

(72) Inventors: Larry Lien, Solana Beach, CA (US); James M. Tranquilla, Lower Queensbury (CA); Tony Picaro, Tarragindi (AU)

(73) Assignee: Eco Technol Pty Ltd, Dalkeith, Perth (AU)

( * ) Notice: Subject to any disclaimer, the term of this patent is extended or adjusted under 35 U.S.C. 154(b) by 0 days.

(21) Appl. No.: 13/736,758

(22) Filed: Jan. 8, 2013

(65) Prior Publication Data
US 2013/0131199 A1     May 23, 2013

Related U.S. Application Data

(63) Continuation of application No. PCT/US2011/042365, filed on Jun. 29, 2011.

(60) Provisional application No. 61/362,975, filed on Jul. 9, 2010.

(51) Int. Cl.
   *C07C 27/00*     (2006.01)

(52) U.S. Cl.
   USPC ............ 518/700; 518/702; 518/703; 518/704

(58) Field of Classification Search
   USPC ......................................... 518/700, 702–705
   See application file for complete search history.

(56) References Cited

U.S. PATENT DOCUMENTS

| | | | |
|---|---|---|---|
| 4,529,411 A | 7/1985 | Goddin, Jr. et al. | |
| 4,975,164 A | 12/1990 | Ravella et al. | |
| 5,266,175 A | 11/1993 | Murphy | |
| 5,277,773 A | 1/1994 | Murphy | |
| 5,411,721 A | 5/1995 | Doshi et al. | |
| 5,621,155 A | 4/1997 | Benham et al. | |
| 5,763,716 A | 6/1998 | Benham et al. | |
| 5,993,761 A | 11/1999 | Czernichowski et al. | |
| 6,153,852 A | 11/2000 | Blutke et al. | |
| 6,248,794 B1 | 6/2001 | Gieskes | |
| 6,572,678 B1 | 6/2003 | Wijmans et al. | |
| 6,579,331 B1 | 6/2003 | Ho | |
| 6,596,780 B2 | 7/2003 | Jahnke et al. | |
| 6,976,362 B2 | 12/2005 | Sheppard et al. | |

(Continued)

FOREIGN PATENT DOCUMENTS

WO     WO 01/79754 A1     10/2001

OTHER PUBLICATIONS

Rezaei et al.; "Syngas Production by Methane Reforming with Carbon Dioxide on Noble Metal Catalysts"; Journal of Natural Gas Chemistry; 2006; pp. 327-334.

*Primary Examiner* — Jafar Parsa
(74) *Attorney, Agent, or Firm* — Fitch, Even, Tabin & Flannery LLP (57) ABSTRACT

Streams (11) of natural gas contaminated with significant amounts of carbon dioxide can be efficiently and economically processed to create Syngas (16). An available source (1) of flue gas that might otherwise be dispersed into the atmosphere in conjunction with such a $CO_2$-laden natural gas stream (11) renders the process even more economical and efficient through the creation of multiple feedstreams (14, 27, 34) that are combined to deliver a composite near equal mixture of methane and $CO_2$ to a plasma reactor (15) or the like that will generate Syngas. When coupled with a Fischer-Tropsch reactor (40), the overall process provides a particularly efficient and economical process for producing synthetic liquid hydrocarbons.

16 Claims, 4 Drawing Sheets

(56) References Cited

U.S. PATENT DOCUMENTS

| | | |
|---|---|---|
| 7,153,344 B2 | 12/2006 | Filippi et al. |
| 7,314,503 B2 | 1/2008 | Landrum et al. |
| 7,588,746 B1 | 9/2009 | Muradov et al. |
| 7,648,566 B2 | 1/2010 | Wei et al. |
| 7,666,381 B2 | 2/2010 | Henderson et al. |
| 7,686,856 B2 | 3/2010 | Hemmings et al. |
| 2005/0180907 A1 | 8/2005 | Holcomb et al. |
| 2006/0163054 A1 | 7/2006 | Spitzl et al. |
| 2006/0230935 A1 | 10/2006 | Michael et al. |
| 2007/0049647 A1 | 3/2007 | Van Egmond et al. |
| 2008/0134660 A1 | 6/2008 | Finkenrath et al. |
| 2008/0272340 A1 | 11/2008 | Koh |
| 2009/0100752 A1 | 4/2009 | Sessa et al. |
| 2010/0154641 A1 | 6/2010 | Kase et al. |

SYNGAS PRODUCTION THROUGH THE USE OF MEMBRANE TECHNOLOGIES

This application is a continuation of International Patent Application No. PCT/US2011/042365, filed Jun. 29, 2011, which claims priority from U.S. Provisional Application Ser. No. 61/362,975, filed Jul. 9, 2010, the disclosures of both of which are incorporated herein by reference.

The present invention relates generally to the formation of Syngas ($CO+H_2$), and more particularly, it relates to the control and regulation of supplies of carbon dioxide and methane with membrane technology to provide an appropriate feedstream for Syngas production. Still more particularly, it relates to the use of membrane technologies in the separation of carbon dioxide from carbon dioxide contaminated gases to provide innovative mixtures with methane having ratios of carbon dioxide and methane suitable for reformation and transformation into Syngas and additionally to employing such Syngas as a feedstock that is converted to liquid hydrocarbons in a Fischer-Tropsch (F-T) reactor.

BACKGROUND OF THE INVENTION

The subject of carbon dioxide management is paramount in the overall strategy of greenhouse gas reduction. Carbon dioxide management in this context can include reduction, containment and conversion, as well as combinations of these approaches. While reduction of new carbon dioxide emissions is critical in any future anti-climate-change environmental strategy, it does not address the enormous inventory of present carbon dioxide in the ecosystem, nor does it address the current momentum of generating new emissions. For that reason, there is an important emphasis on developing technologies that can efficiently capture carbon dioxide (preferably at point discharge sites) and use it as part of a regeneration cycle for new fuel sources.

The use of semipermeable membranes for effecting gas separations has become well accepted, and membranes of various polymeric and inorganic configurations display various degrees of separation, across a broad spectrum of gases and gas mixtures. Such semipermeable membranes are available in flat sheet, tubular, spiral wound and hollow fiber configurations, and many membranes exhibit good separation factors, i.e. 2.5-50 to 1 for carbon dioxide and methane, and 2.5-100 to 1 for $CO_2$ and nitrogen, as well as high permeabilities at fairly low net driving pressures. If these strategies are to be successful, it may often be required to be able to accept a variation of feed inputs and then process them so as to control and regulate the gaseous mixtures to obtain a desired mixture of carbon dioxide, methane and/or nitrogen for supply to a subsequent process.

As mentioned above, carbon dioxide capture is only part of an effective carbon dioxide management strategy; an important part is providing an efficient means of converting the carbon dioxide into high value fuel (and non-fuel) products, as such will alleviate the need to bring new carbon into the overall fuel cycle. Generally, carbon dioxide conversion has proven to be an energy-intensive process, and such can negate an overall objective of energy efficiency. Plasma technology, however, has emerged as one approach for the efficient conversion of carbon dioxide, particularly in gas mixtures where hydrogen source gases are present. Microwave plasmas are particularly efficient in these processes, with reported energy costs as low as 0.15 kWh per cubic meter of hydrogen gas produced from the reformation of methane and carbon dioxide.

Dickman et al U.S. Pat. No. 7,682,718 discloses a fuel management system for a hydrogen fuel cell; the system comprises a number of tanks that can be controllably filled and mixed from a variety of feeds as part of the required fuel mix for the fuel cell. Adamopoulos et al U.S. Pat. No. 7,637,984 uses an adsorbent material to first remove sulfur from a gas stream which is then treated with a membrane system to separate carbon dioxide from a hydrogen-rich stream.

Wei et al U.S. Pat. No. 7,648,566 mentions the use of inorganic and polyether membrane systems for the purpose of separating carbon dioxide from a Syngas stream in order to produce an enriched hydrogen stream as a part of a pre-combustion carbon dioxide capture process. Muradov et al U.S. Pat. No. 7,588,746 mentions possibly using a membrane system, a pressure swing adsorption system or a cryogenic adsorption unit for treating combustion gas from hydrogen combustion to separate hydrogen from other gases (including methane).

Hoffman et al U.S. Pat. No. 7,634,915 suggests that zeolite and ceramic membranes may be used to separate a carbon dioxide rich stream from a carbon dioxide lean stream (where the carbon dioxide lean stream may contain carbon monoxide, nitrogen and unspent fuel such as methane) as a part of a turbine system for producing hydrogen and isolating carbon dioxide. In this system, the carbon dioxide is used for combustion temperature regulation and turbine cooling. Hemmings et al U.S. Pat. No. 7,686,856 discloses a system for Syngas production using water and methane reforming; in this system, an oxygen transport membrane is used as part of the combustion process to produce the Syngas products. Murphy U.S. Pat. No. 5,277,773 discloses a microwave plasma used for a reformer reaction including water and a hydrocarbon where the plasma reaction is initiated using one or more metallic wire segments.

It is known that microwave plasma technology can be used to reform gas streams which contain specific concentrations of $CO_2$ and $CH_4$ with a mole ratio of not greater than about 1.5 to 1, i.e. carbon dioxide (in the range of 40-60 mole percent) and methane (in the range of 60-40 mole percent), into a carbon monoxide and hydrogen (Syngas) mixture (see U.S. Pat. Nos. 4,975,164 and 5,266,175). Such a product can be used as a feedstock for a conventional Fischer-Tropsch (F-T) synthesis (see U.S. Pat. Nos. 6,596,780 and 6,976,362, the disclosures of which are incorporated herein by reference) that will convert such a gaseous mixture to liquid hydrocarbons. However, it is most important that efficiencies in operation be found before such strategies can become an economic reality.

Notwithstanding the advancement in both the areas of membrane technology and plasma technology, there is a present need for the integration of these technologies in a manner which renders such membrane separations able to function as useful, "tunable" elements in an integrated gas management system and plasma reformer process. In particular, there is a need for a membrane-based gas control system that is capable of providing an optimum gas mixture feedstream, created from a variety of carbon dioxide sources, to a microwave plasma reformer.

Accordingly, it is one of the objectives of the present invention to provide a membrane-based system that can capture carbon dioxide directly from a variety of sources, concentrate it, combine such concentrate with methane gas, and controllably and economically create an optimum gas mixture for use as a feedstream to a microwave plasma reformer for the production of Syngas.

It is another objective of the present invention to provide a process and system that, in addition to the above, can co-generate sufficient electrical energy to power such a microwave plasma reformer.

It is yet another objective of the present invention to provide a process as set forth above integrated in combination with a Fischer-Tropsch liquid hydrocarbon production process.

SUMMARY OF THE INVENTION

It has been found that separation/concentration of carbon dioxide and methane using membrane technologies can be combined with power production to economically provide specific mole ratios of carbon dioxide and methane useful as feedstream to a microwave plasma process that economically produces a carbon monoxide and hydrogen mixture commonly referred to as Synthesis gas, i.e. Syngas. The system preferably includes an electrical cogeneration feature that will supply most or all of the energy necessary for the plasma reformer operation. In some embodiments, the membrane separation processes are integrated to also assist in the recovery of energy from a Fischer-Tropsch process which receives the Syngas as a feedstock; such energy is then used to supplement the energy required for the plasma reformer and/or the membrane separation processes.

Systems are provided which convert carbon dioxide and methane into Syngas, a $CO-H_2$ mixture that is a common feedstock used in the production of higher fuel products, such as diesel fuel and other liquid hydrocarbons. The systems include components which capture, separate and concentrate selected input gas streams and then convert them into Syngas by means of a plasma reformer reactor or the like, as described in U.S. Pat. Nos. 4,975,164; 5,266,175; 5,277,773; 5,621,155; 5,993,761 and 6,153,852, the disclosures of which are incorporated herein by reference.

A benefit of the plasma technology is that it has very small footprint requirements because the conversion reaction occurs in a matter of seconds or less, and that it can be operated as a continuous process. Considering that a 1000 MW coal-fired power station may emit approximately 800-1000 tons/hour of $CO_2$, then a simple and continuous process with a very short residence time is ideally suited for carrying out the conversion reaction. This makes the plasma conversion approach an ideal way to manage carbon emission from large point source emitters like power stations and industrial sites such as cement mills or steel mills.

Such systems are controllable to accept a fairly wide range of input gas concentrations and mixtures while providing a desired gas mixture for a particular reformer, and it may also be feasible to re-circulate any gas imbalance without releasing greenhouse gases to the atmosphere. As mentioned above, it is also desirable to include an electrical cogeneration feature which can supply most or all of the energy necessary for the operation which would include the average plasma reformer.

Advantages of the overall process include climate change mitigation as a result of concentrating (removing 90+%) of the post combustion carbon dioxide from a fossil fuel, e.g. hydrocarbon or coal-based, gas stream associated with electric power production. Generally, the process, using membrane technology and process recirculation, will concentrate carbon dioxide normally released into the atmosphere from such anthropological sources and concentrate it; such concentrated carbon dioxide then subsequently becomes a part of a feed source for microwave plasma reformation (or other transformational process).

In one particular aspect, there is provided A process for producing Syngas in a plasma or chemical reformation device from a flue gas stream and a natural gas stream, which process comprises providing a flue gas stream from a carbon or hydrocarbon combustor and separating such stream in a first semipermeable membrane device into a first predominantly $CO_2$ stream and a second stream containing predominantly $N_2$, providing a natural gas stream that contains $CH_4$ and between about 2 and 40% $CO_2$ and separating such stream in a second semipermeable membrane device to provide a first feedstream that is increased in $CO_2$ content and contains $CO_2$ and $CH_4$ in an about 50/50 molar ratio (as defined herein) and a third stream containing at least about 90% methane, blending a first substream from said third stream with said first predominantly $CO_2$ stream to create a second feedstream containing $CO_2$ and $CH_4$ in an about 50/50 molar ratio, combusting a second substream from said third stream with air in a cogeneration apparatus to produce electrical power, delivering an exhaust gas stream from the cogeneration apparatus to a third semipermeable membrane device and separating a second predominantly $CO_2$ gas stream, and blending said second predominantly $CO_2$ stream with a third substream of said third stream to create a third feedstream containing $CO_2$ and $CH_4$ in an about 50/50 molar ratio, and delivering a composite feedstream made up of said first, second and third feedstreams to the plasma or chemical reformation device which converts such to Syngas, whereby Syngas is produced in an environmentally friendly process from natural gas and a flue gas stream, which process is controlled to generate sufficient electric power to operate said first, second and third membrane separation devices and said plasma or chemical reformation device.

In another particular aspect, there is provided a process for producing Syngas in a plasma or chemical reformation device from a natural gas stream containing a significant quantity of $CO_2$, which process comprises providing a natural gas stream that contains $CH_4$ and between about 2 and 40% $CO_2$ and separating such stream in a semipermeable membrane device to provide a first permeate stream that is increased in $CO_2$ content and contains $CO_2$ and $CH_4$ in an about 50/50 molar ratio (as defined herein) and a methane-rich concentrate stream containing at least about 90% methane, combusting a substream from said concentrate stream with air in a cogeneration apparatus to produce electrical power, delivering an exhaust gas stream from said cogeneration apparatus to another semipermeable membrane device and separating a predominantly $CO_2$ permeate stream, blending said predominantly $CO_2$ permeate stream with another substream of said methane-rich concentrate stream to create a feedstream containing $CO_2$ and $CH_4$ in an about 50/50 molar ratio, and delivering a composite feedstream made up of said first permeate stream and said feedstream to a plasma or chemical reformation device which converts such to Syngas, whereby Syngas is produced in an environmentally friendly process from $CO_2$-containing natural gas, which process is controlled to generate sufficient electric power to operate said membrane separation devices and said plasma or chemical reformation device.

In a further particular aspect, there is provided a process for producing Syngas in a plasma or chemical reformation device from a natural gas stream containing a significant quantity of $CO_2$, which process comprises providing a natural gas stream that contains $CH_4$ and between about 2 and 40% $CO_2$ and separating such stream in a semipermeable membrane device to provide a first permeate stream that is increased in $CO_2$ content and contains $CO_2$ and $CH_4$ in an about 50/50 molar ratio (as defined herein) and a methane-rich concentrate stream containing at least about 90% methane, combusting a substream from said concentrate stream with air in a cogeneration apparatus to produce electrical power, delivering an exhaust gas stream from the cogeneration apparatus to another semipermeable membrane device and separating a predominantly $CO_2$ permeate stream, blending said predominantly $CO_2$ permeate stream with another substream of said concentrate stream to create a feedstream containing $CO_2$ and $CH_4$ in an about 50/50 molar ratio, delivering a composite feedstream made up of said first permeate stream and said feedstream to a plasma reformation device which converts such to a first Syngas product stream, splitting a third substream from said concentrate stream and feeding such to a second plasma reformation device as a mixture with steam and/or water to convert such mixture to a second Syngas product stream of a higher hydrogen content, and combining said first and second Syngas product streams whereby Syngas having a relatively high hydrogen content is produced in an environmentally friendly process from natural gas, which process is controlled to generate sufficient electric power to operate said membrane separation devices and both said plasma reformation devices.

DETAILED DESCRIPTION OF THE PREFERRED EMBODIMENTS

Semipermeable membrane technology is used in the various illustrated processes to regulate and control particular gas streams in the overall system, e.g. by removing carbon dioxide from a flue gas exhaust from gasoline, diesel, coal or natural gas fired combustor/power generator, concentrating such carbon dioxide and subsequent blending such with an external source of methane to produce a mixed gas stream having a desired $CO_2/CH_4$ ratio for an inflow stream to a plasma reformer to create Syngas. Many feel that power plant operations which generate carbon dioxide by the combustion of various carbonaceous fossil fuels are creating harmful greenhouse gases that are normally being released into the atmosphere. Although energy is required to recover these gases, the amount of energy required to drive these membrane separation processes is minimized, as by pressurizing the flue gas with a blower and then removing the volume of gas permeating through a membrane, i.e. concentrated carbon dioxide, using a vacuum.

Very generally, a flue gas feed source will be fed to a membrane separation device which produces concentrated carbon dioxide as a permeate. In a single pass, the amount of carbon dioxide exiting the concentrate side of the membrane may include a major amount of the original mass of carbon dioxide in the flue gas stream; however, additional stages can be used when desired. A membrane is preferably chosen for flue gas concentration that has a selectivity for carbon dioxide to nitrogen (the primary gas in such exhaust gas streams) of at least about 10-15 to 1. Polymeric membrane gas separation devices are generally imperfect, and a permeate stream from flue gas may include about 70% $CO_2$ and about 30% $N_2$. Should the plasma reformer require less $N_2$, a second stage can reduce the $N_2$ to 5-10%, and a third stage to about 2%. The ratio of permeate gas produced to input stream can also be controlled when using polymeric membranes by selecting the membrane surface thickness used in a spiral wound separation element, for example, or other such membrane device, so that concentration polarization is properly controlled by the length of the leaves; as known in this art, element efficiency is based on that leaf length, and on the volume and velocity of feed stream into the element.

Generally, semipermeable membrane devices will be constructed of membrane materials and will use engineering principles based on the feed gas types and the degree of regulation and control needed to efficiently achieve the desired gas mixtures. Gas separation processes using semipermeable membrane separation device in unique configurations are engineered to specifically regulate and control the amount of carbon dioxide or methane that is removed from a particular feed gas source in order to produce an ultimate, desired mole ratio of carbon dioxide to methane suitable as an inflow stream for reformation and then ultimate transformation into liquid hydrocarbons or other chemicals. Both contaminated natural gas and carbon dioxide-laden flue gas are useful feed sources upon which the present invention focuses to produce feedstreams tailored for a particular microwave plasma process.

This novel approach combining membrane technology and microwave plasma reformation or other similar reformation is expected to be effective in cases where only fairly small amounts of carbon dioxide (0.5-20%) are present in flue or exhaust gas streams, such as those from electric power generation plants fueled by methane, diesel, gasoline or coal combustion, as well as from cement kilns, steel plants and the like, where other methods of $CO_2$ removal and concentration might be prohibitively expensive. Streams containing about 20 to 40% $CO_2$ would of course likewise be useful. Concentration of carbon dioxide using semipermeable membrane technology allows for carbon dioxide to be precisely regulated thereby insuring the desired mix of carbon dioxide and methane is ultimately obtained. Some amount of $N_2$ can usually be tolerated in a feedstream to a plasma reformer, e.g. about 5-30%; moreover, some residual nitrogen may be desired as a sweep-swirl gas, to enhance the downstream microwave plasma-reforming into Syngas. Overall, the processes have huge implications for reducing carbon dioxide emissions from the burning of hydrocarbons, natural gas and coal. The processes are felt to have particular advantages to allow economic use of natural gas deposits contaminated with amounts of carbon dioxide of for example about 5% to 35%; however, streams having about 2% to 40% $CO_2$ may also be beneficially used. Generally, the ability of semipermeable membrane technologies to control and regulate volumes and concentrations of carbon dioxide and methane that permeate a membrane device allows the creation of clean streams of desired mole ratios of carbon dioxide and methane that will be useful as a feedstreams for microwave plasma reactors or the like.

Fundamental to the operation of the systems and processes described herein is the manner by which semipermeable membrane devices operate to provide the necessary and desirable controllable gas separation, particularly to provide specific gas mixtures which have a specified, desired mole ratio of $CO_2$ and $CH_4$. For treatment of natural gas streams, it will be understood by one skilled in this art that although various inorganic, e.g. zeolite, and organic membranes may be used, polymeric semipermeable membranes will likely be chosen to separate $CO_2$ and $CH_4$. Polymeric membranes have been known to be useful for gas separation purposes for some time and may be formed from polymers such as polydimethylsilicone (PDMS), polyimides, polyarylethers, polyarylketones, polycarbonates, polysulfones, and polyacetylenes. Such semipermeable membranes, many of which are $CO_2$-selective, are disclosed in U.S. Pat. Nos. 4,529,411; 5,411,721; 6,572,678; 6,579,331; and 7,314,503, the disclosures of which are incorporated herein by reference. Polymeric membranes are preferably used that will preferentially permeate carbon dioxide in the ratio of about 3-6 parts carbon dioxide to one part methane when treating a natural gas stream containing between about 2 and 40 mole % $CO_2$ based upon total moles of $CO_2+CH_4$. By use of multiple stages in such a device, if needed, a permeate gas ratio is controlled within a desired range of values by selecting suitable membrane surface thickness and overall device design for spiral wound membrane sheet elements, for example as mentioned before, taking concentration polarization into consideration. In addition, net driving pressures are appropriately controlled for each membrane separation device used by controlling the feed, permeate and concentrate pressures; as a result, one can ensure that the desired mole ratio of carbon dioxide and methane is permeated.

For combustion flue gases it will be understood by one skilled in this art that the semipermeable membrane of choice will preferentially permeate a predominantly carbon dioxide stream, e.g. in the ratio of at least about 5-50 parts carbon dioxide to one part nitrogen. If certain residuals are present that might be detrimental to the subsequent plasma reforming process, $SO_x$ for example may be preliminarily removed from the flue gas stream by adsorption. Often small amounts of NOx can be tolerated in the feedstream. The final permeate gas ratio is generally achieved within a range of acceptable $N_2$ content by selecting the membrane surface thickness and adjusting the concentration polarization factors as discussed above. Likewise, net driving pressure is controlled by controlling the feed, permeate and concentrate pressures to ensure that the resultant predominantly carbon dioxide permeate stream has no more than an acceptable minor amount of $N_2$.

These semipermeable membrane devices are constructed using materials and engineering principles known in this art to achieve the degree of gas separation desired for each specific separation operation. The membrane devices may include multiple stages connected in appropriate configurations that can be specifically regulated and controlled, with multiple permeation steps if needed, to produce the desired gas concentrations.

The combination of such membrane separation processes and a plasma reforming process with an integrated electrical power cogeneration feature that supplies most or all of the energy necessary for the plasma reforming operation and the membrane separation processes creates a most economical and efficient stand-alone system. In addition, the further integration of a Fischer-Tropsch reactor allows still further economy of overall operation via the recovery of energy from the Fischer Tropsch process. In this way, it is possible to capture all or the majority of $CO_2$ emissions resulting from a combustor that burns natural gas to provide electrical energy for the operation, with the captured $CO_2$ providing up to about one-half of the feedstock/reactants required for producing synthetic fuel. As a result, it is possible to significantly increase the amount of Synfuel that can be produced from a given amount of natural gas. Assuming a natural gas inflow stream already contains some percentage of $CO_2$ (e.g. about 2 to 40%), then methane is separated in a first step to provide a permeate having an increased mole ratio of $CO_2$:$CH_4$, namely a composition as desired to provide one portion of a composite stream that can be efficiently converted to Syngas when fed to a plasma reformer. In a conventional GTL process, the $CO_2$ impurity present in the natural gas would need to be either removed, e.g. using solvent absorption, before being fed to a catalytic reforming process, or it might just be allowed to pass through the reformer where it would not take part in the reaction. In contrast, $CO_2$ in the present system contributes an important part of the carbon that is converted to fuel in the plasma reformer; therefore, the $CO_2$ both contributes to the production of additional synthetic fuel and is not potentially detrimentally released to the environment. Overall, it is possible to significantly reduce the amount of $CO_2$ that is emitted to the atmosphere, compared to a conventional GTL plant producing Synfuel from natural gas, while at the same time increasing the amount of synthetic fuel that can be produced from a given amount of methane.

Figure 1:
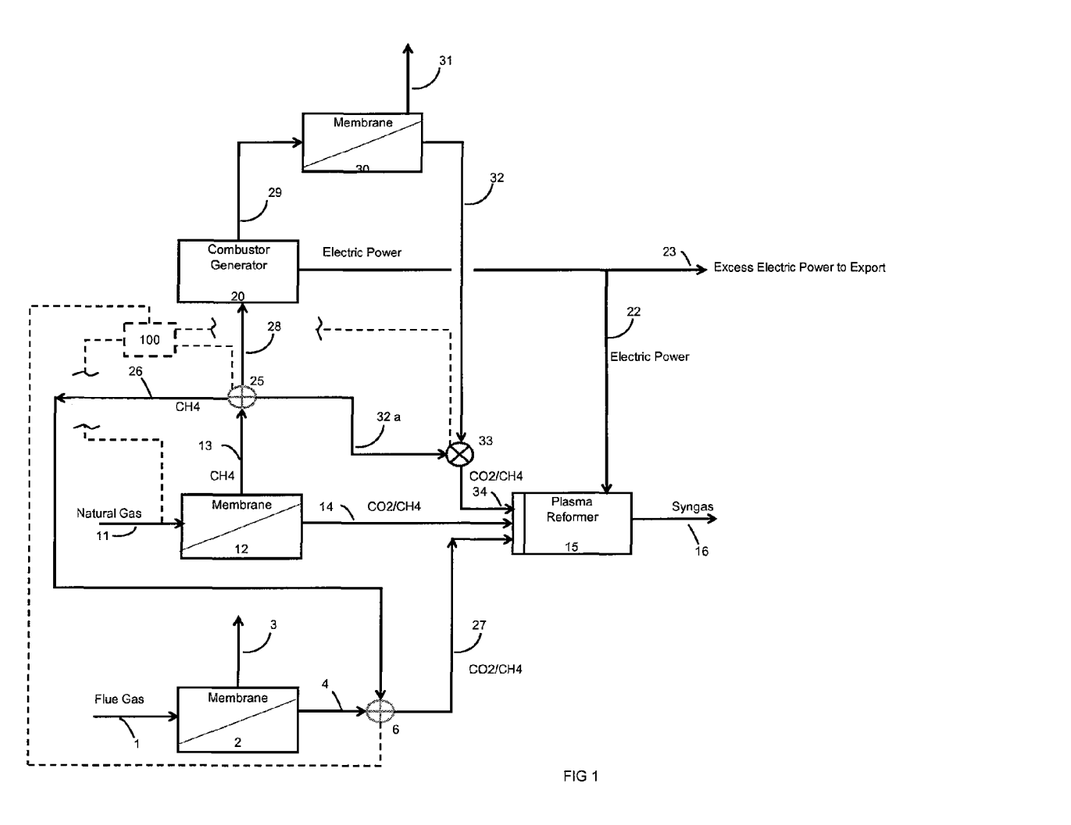
FIG. 1 is a schematic flow sheet illustrating a process embodying various features of the invention wherein a natural gas inflow stream containing methane contaminated by $CO_2$ and a flue gas stream from an energy-producing power plant or other combustor is processed using membrane technologies to produce feedstreams for a Syngas microwave plasma reformer as a part of a co-generation operation that allows the overall system to run without the importation of any electrical power and will likely even allow some export of electrical power.

A process for producing Syngas from a flue gas stream and a $CO_2$-containing natural gas stream which embodies various features of the present invention is shown in FIG. 1 as a schematic flow sheet. The illustrated system would receive a flue gas stream 1 from some combustor of fossil fuel, such as coal, oil or natural gas, or from diesel or gasoline engines or the like; such might in many instances be a flue gas stream from a power plant for the production of electrical power which would have a fairly constant output. Such a flue gas stream from a boiler-operated power plant or from a kiln or the like, fueled by air-oxidation, would include a major portion of nitrogen together with $CO_2$, nitrogen oxides (NOx), sulfur oxides (SOx) and other minor gaseous components. Such flue gas steam, which would otherwise be likely vented to the atmosphere, is used as a carbon dioxide source in the present process. The stream 1 is fed at appropriate temperature and pressure to a first membrane separation device 2, which is depicted in the lower left hand region of FIG. 1. For carbon dioxide separation from flue gas, containing a major portion of nitrogen, various membrane separation systems may be employed; membranes are preferably chosen that would exhibit a preference for $CO_2$ over $N_2$ of at least about 5 to 1 and more preferably, at least about 10 to 1. Polydimethylsilicone (PDMS) membranes may be particularly preferred, and such membranes can be provided in various thicknesses, for example between about 0.1 micron and 10 microns. They are commonly supported on a porous polymeric supportive layer of polysulfone, polyethylene, PVC, cellulose nitrate and the like, e.g. polysulfone UF membranes, or other porous materials such as etched metals and ceramics, e.g. etched aluminum.

The first membrane device 2 may include 1-3 stages and ultimately creates two streams, a permeate stream 4 that comprises predominantly carbon dioxide, with minor amounts of NOx, SOx and a tolerable amount of $N_2$, and a concentrate stream 3. The concentrate stream 3 comprises predominantly nitrogen with some residual amounts of primarily $CO_2$, NOx, and SOx, usually at least about 80 volume percent $N_2$. This stream 3 can be vented to the atmosphere, treated or otherwise disposed of according to available methods. The permeate stream 4 containing predominantly carbon dioxide, e.g. at least about 60 volume percent, preferably at least about 70%, more preferably at least about 80% and most preferably at least about 90%, is directed to a flow regulator/blender 6.

The other incoming stream is a stream 11 of natural gas containing primarily carbon dioxide and methane. For example, it may contain between about 3% to 35% $CO_2$ or between about 2% to 40% $CO_2$, with the remainder being substantially all methane. This stream 11 is delivered to a second membrane separation device 12, which also produces a concentrate stream 13 and a permeate stream 14. As mentioned above, the second membrane device 12 may also include multiple stages of membrane separation. It also can use various different gas separation membranes as known in this art; the membranes chosen should have a preference for $CO_2$ over $CH_4$ of at least about 2 to 1 and preferably at least about 4 to 1. Polymeric membranes, such as those of the classes mentioned hereinbefore, are preferred, and most preferred are PDMS membranes. They would usually be supported on a porous base layer, as described above, if employed in sheet or tubular form for example. The primarily methane natural gas inflow stream 11 is exposed in the second membrane separation device 12 to a polymeric semipermeable membrane that is selective for $CO_2$ in preference to $CH_4$. When treating an inflow that contains a major amount of $CH_4$, the device produces a permeate stream that has an increased amount of $CO_2$ (relative to the inflow natural gas stream 11) and that contains carbon dioxide and methane at a mole ratio not more than a 50% excess of either component. For some plasma reformation processes, an excess of carbon dioxide may be desired, while for others, a methane excess may be desired. The permeate stream may also contain tolerable small amounts of other gases such as nitrogen, usually not more than about 10 volume % and preferably not more than about 5%. The permeate stream 14 having the desired mole ratio of $CO_2$ and methane is delivered as one feedstream to a plasma reformer 15 to be discussed hereinafter.

The concentrate stream 13 from the second membrane separation device 12 is predominantly methane, usually about 90 to 99 volume %, preferably at least about 96% and more preferably at least about 98%, with the remainder primarily $CO_2$. It is directed to a flow regulator 25 that splits the stream 13 into 3 substreams under the control of a control system 100. A first substream 26 from the flow regulator 25 is directed to the blending regulator 6 where it is mixed with the predominantly $CO_2$ stream 4 exiting the first membrane separation device so as to produce a blended stream 27 that is directed as another feedstream to the plasma reformer 15 where it is mixed with the permeate stream 14. The blending at the regulator 6 is such that the carbon dioxide and methane mole ratio is likewise not more than a 50% excess of either.

A second substream 28 is fed to a combustor-generator 20, such as an internal combustion engine or a turbine which drives an attached electrical generator, to generate electrical power by burning methane with air, which results in the creation of carbon dioxide and water vapor. The exhaust gas stream 29 from the combustor-generator 20 is directed to a third membrane separation device 30 which may have characteristics similar to the first membrane separation device 2. The device 30 produces a permeate stream 32 that is predominantly $CO_2$ with tolerable concentrations of NOx, SOx, and $N_2$. The concentrate stream 31, comprising predominantly nitrogen, is handled in the same manner as the concentrate stream 3, i.e. by exhaust to the atmosphere or further treatment. The predominantly $CO_2$ permeate stream 32 is fed to another regulator/blender 33 to which the third substream 32a from the regulator 25 is also delivered. The regulator-blender 33 mixes the streams 32 and 32a to produce yet another feedstream 34 for delivery to the reformer wherein carbon dioxide is again present in a mole ratio to methane of between 0.67 to 1 and 1.5 to 1. This blended feedstream 34 is mixed along with the feedstreams 14 and 27 to provide a composite feedstream that is delivered to the plasma reformer 15. The composite feedstream contains $CO_2$ and $CH_4$ in about equal mole amounts or at a ratio where one does not exceed the other by more than 50%; this mole ratio is loosely referred to herein as an about 50/50 ratio.

The control system 100 regulates the overall process by controlling the compositions and the various flow rates so that the composite feedstream has the desired composition for the plasma reformer 15, e.g. equal moles of $CO_2$ and $CH_4$ or usually within about 2-5% of equal. However, if desired for a particular reformation process, a 20% or 30% or higher molar amount of either $CO_2$ or $CH_4$ might be present in a particular composite feedstream. By monitoring the flows of the three feedstreams 14, 27 and 34 and controlling the amount of inflow of the natural gas stream 11 and the regulators 6, 25 and 33, a composite feedstream of desired composition is fed to the plasma reformer by the control system 100. For example, blender/regulators 6, 33 might each be connected to a separate channel of a gas chromatograph (GC) with interface to a computer control system 100, so as to control the amounts of $CH_4$ and $CO_2$, exiting the regulators via a hydraulic or pneumatic valve system that is also associated with the regulator 25 and an inlet valve in the incoming natural gas line 11. The membrane separation devices may be connected to other channels of the GC and appropriately controlled by operation of multiple stages and/or recycling therewithin. Instructions and overall control are programmed into a CPU associated with the main control system 100.

The plasma reformer 15 can utilize the plasma technology that has emerged in the last decade as an efficient process for the conversion of carbon dioxide, in a gaseous mixture containing a source of hydrogen, to produce Syngas (a mixture of hydrogen and carbon monoxide). Methane and/or water are commonly used as a hydrogen source. Alternatively, chemical transformation devices which rely upon catalytic action may be used to likewise convert a gaseous mixture comprising mainly carbon dioxide and methane (in a mole ratio of not greater than about 1.5 to 1). Such chemical transformation devices are variously shown in U.S. Pat. Nos. 5,621,155 and 5,763,716, and described in Rezaei, M., S. M., Alavi, S., Sahebdelfar and Zi-Feng Yan, (2006), "Syngas production by methane reforming with carbon dioxide on noble metal catalysts", *Journal of Natural Gas Chemistry*, Vol. 15, pp. 327-334.

Preferably, plasma reformers are used, and more preferable are those plasma reformers that rely on microwave energy to create the plasma as they are capable of operation at relatively low energy cost and can be operated as a continuous flow process through the reactor. Such microwave type plasma reactors are shown in U.S. Pat. Nos. 5,266,175 and 5,277,773, and as known in this art, plasma reactors of this type can be used to produce Syngas from gas feed streams containing $CO_2$ and methane in the previously stated about 50/50 mole ratio. Such a microwave energy plasma reformer 15 can be supplied with sufficient electrical power from the combustor-generator 20 as indicated in the flow sheet by the schematic distribution line 22. In addition, the electrical power generated can be used to drive the auxiliary blowers, compressors and other machinery to operate the three membrane separation devices 2, 12 and 30. It is expected that all of this can be accomplished without requiring power from a power plant that may be supplying the flue gas stream 1. This may be important because the combustor supplying the flue gas stream 1 may be a non-electrical power generator, such as a kiln, a steel mill or some other heat-generating device. Furthermore, depending upon the amount of carbon dioxide needed to mix with the available methane in the substream 32a to create a third feedstream 34 of $CO_2$/methane for delivery to the plasma reformer 15, it may be practical to generate some excess electrical power using the combustor-generator 20, and such power could then be marketed.

The output from the plasma reformer 15 is a continuous stream of Syngas comprising a mixture of primarily carbon monoxide and hydrogen. The output ratio will vary slightly depending upon the precise ratio of the about 50/50 mixture of the feed streams being supplied to the plasma reformer. If a higher mole ratio of carbon dioxide is present in the combined feed streams, then the Syngas may include a greater percentage of CO and a smaller percentage of hydrogen. As mentioned above, the control system 100 is utilized to control and regulate the flow regulator/blenders 6 and 33, the regulator 25 and the inflow of natural gas in the line 11 while monitoring the compositions and flow rates of the three feedstreams so that the overall system operates continuously to provide a composite feedstream within the desired mole ratio. Thus, the process efficiently tracks the flue gas inflow to fully utilize it as its primary $CO_2$ source, making adjustments as needed to present three feedstreams that are mixed to provide a composite feedstream of desired character that is fed to the plasma reformer 15.

Figure 2:
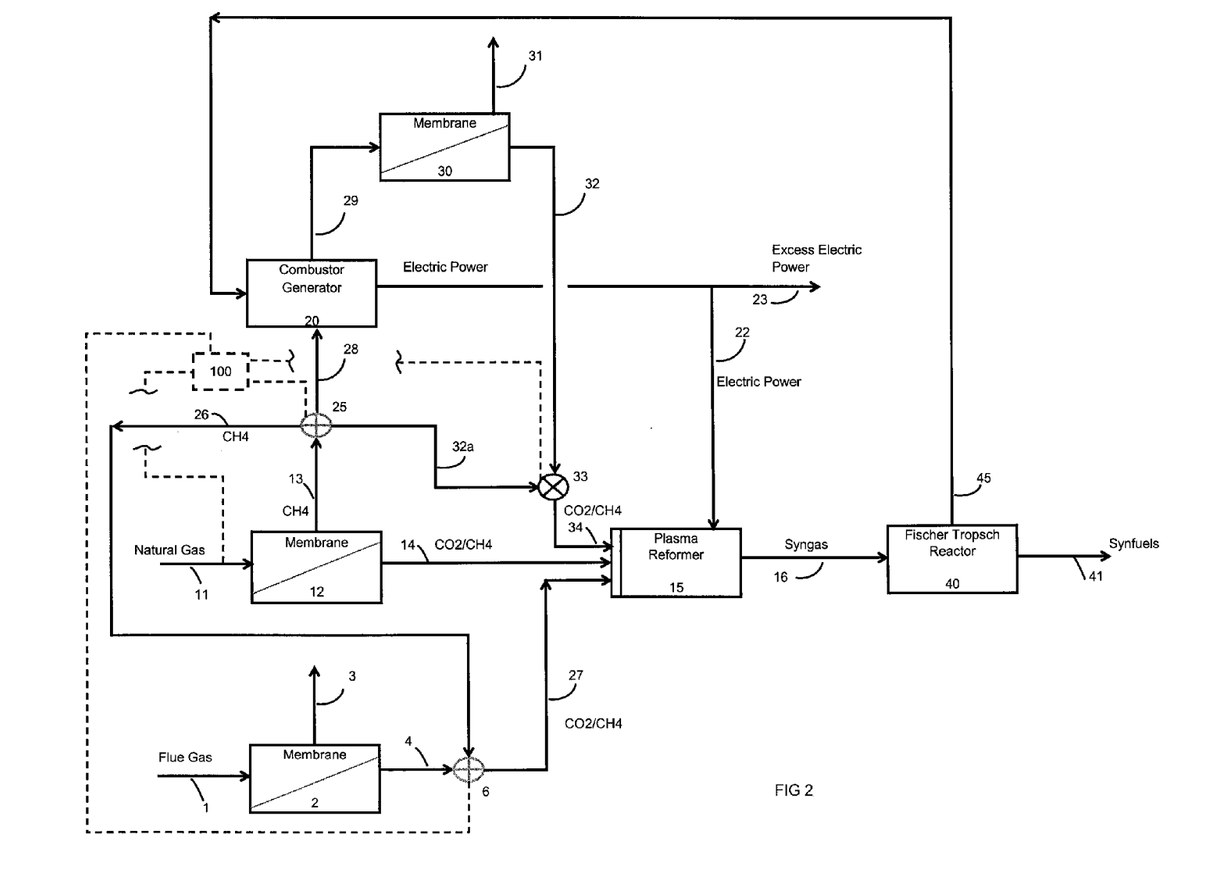
FIG. 2 is a schematic flow sheet of a process similar to that shown in FIG. 1, which is also operated in conjunction with an existing power plant or combustor, wherein the Syngas output is fed to a Fischer-Tropsch reactor for the creation of liquid hydrocarbons while the byproducts and heat from the F-T reactor are recovered and used to assist in the creation of co-generated electrical power.

Although there are various uses for Syngas as well known in this art, the process described above can be advantageously coupled with a Fischer-Tropsch (F-T) reactor that will generate synthetic liquid hydrocarbons from a Syngas feedstock of this character, which synthetic hydrocarbon mixtures are sometimes referred to as Synfuels. Depicted in FIG. 2 is a further process embodying various features of the present invention which incorporates an F-T reactor 40 as a final stage in such an overall process. The primary portion of the process is carried out as described just above with respect to FIG. 1. The exit stream 16 of Syngas is delivered to an F-T reactor 40.

An F-T reactor or F-T synthesis utilizes a known set of chemical reactions that effectively convert a mixture of carbon monoxide and hydrogen into liquid hydrocarbons. The F-T synthesis has become a key component of gas-to-liquid fuel technology and produces a petroleum substitute. The desirable products from the F-T synthesis are primarily alkenes and/or alkanes. The F-T reactions are generally carried about at temperatures between about 150° and 300° C. and at relatively high pressures. Fischer-Tropsch reactors are well-known, and examples are described in the U.S. patents mentioned hereinbefore. The compressors needed to provide the required pressure can be supplied with electrical power from the combustor-generator 20; many of the chemical reactions, once operating, are exothermic and provide heat and some carbon dioxide. Moreover, an otherwise troublesome by-product of F-T, i.e. carbon dioxide, can be used to advantage when incorporated into such a process such as that of FIG. 1. In FIG. 2, the F-T reactor byproducts including heat and $CO_2$, as well as any unreacted $H_2$, $CH_4$ and/or CO, are schematically depicted by the line 45 indicating that they are being recycled to the combustor-generator 20 where they are effectively used to provide additional combustibles, additional $CO_2$ for delivery through the line 29 to the third membrane separation device, and heat for use in conjunction with a gas turbine generator or the like to produce additional electrical power.

Overall, the control system 100 assures that efficient continuous operation is afforded as explained above. The control system 100 monitors the amount of methane being separated as the concentrate stream 13 and splits the stream into the three substreams at the regulator 25. A sufficient amount of natural gas is caused to be supplied through the line 11 to the second membrane device 12 so that the concentrate stream 13 will be sufficient to provide sufficient methane to fulfill the desired functions of the substreams 26, 28 and 32a. More particularly, sufficient methane is supplied to the line 26 to blend with all of the $CO_2$ being obtained from the flue gas stream 1 to provide the feedstream 27 of desired composition which is then mixed with the feedstream 14 that permeates through the membrane separation device 12. In addition, the control system 100 assures that sufficient methane is delivered through the lines 28 and 32a to generate the desired amount of electric power while providing a $CO_2$-containing exhaust stream 29, which will be separated in the third membrane separation device 30 to create the predominantly $CO_2$ stream 32. The third substream 32a is controlled to provide sufficient methane flow to mix in the desired about 50/50 mole mixture with the stream 32 in the regulator/blender 33. The result of this overall process control is such as to feed a composite feedstream of desired composition to the plasma reformer, e.g. within about 2% of a 1:1 ratio of $CO_2$ and $CH_4$. When an F-T reactor 40 is incorporated into the overall system as depicted in FIG. 2, then there will be additional $CO_2$ provided in the inflow stream 29 to the third membrane separation device; thus, the control system 100 may need to provide additional methane in the line 32a leading to the blender/regulator 33 and perhaps also increase the amount of natural gas 11 in the main inflow stream if necessary. As a result, it can be seen that the overall process can very efficiently use a $CO_2$-contaminated natural gas stream and a $CO_2$-containing flue gas stream from a combustor of fossil fuel to effectively and efficiently produce a continuous stream of synthetic hydrocarbons, sometimes referred to as Synfuels.

Figure 3:
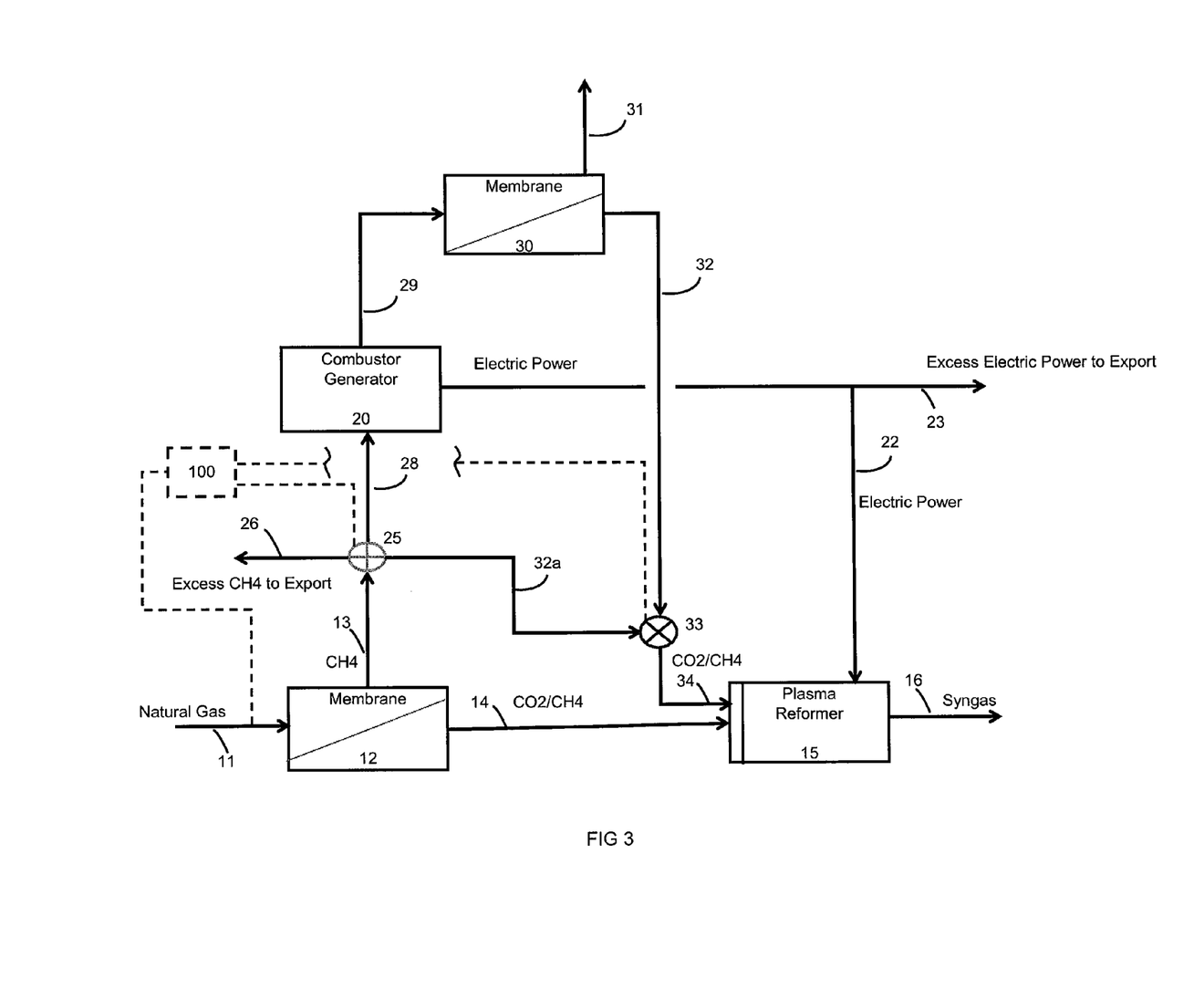
FIG. 3 is a schematic flow sheet illustrating a process embodying various features of the invention wherein a standalone natural gas inflow stream containing methane contaminated by $CO_2$ is processed using membrane technologies to produce feedstreams for a Syngas microwave plasma reformer as a part of a co-generation operation that allows the overall system to run without the importation of any electrical power and will likely even allow some export of electrical power.

Illustrated in FIG. 3 is a further embodiment of a process for producing Syngas from a $CO_2$-containing natural gas stream that embodies various features of the invention. The FIG. 3 embodiment differs from the previously described processes in that it is operated in a location where there is no ready flow of a flue gas stream from a fossil fuel combustor or the like. In the FIG. 3 arrangement, the incoming natural gas stream 11 that contains between about 2% and about 40% carbon dioxide, with the remainder mainly methane, and is similarly delivered to a membrane separation device 12. As described previously, the device 12 separates the inflow to a greater than 90% methane concentrate stream 13 and a permeate stream 14 that contains an increased percentage of $CO_2$ wherein the composition of $CO_2$ and methane is in an about 50/50 mole ratio. The permeate stream 14 is delivered to a transformation device, preferably a microwave plasma reformer 15. The predominantly methane concentrate stream 13 is delivered to a regulator 25 which again divides the total flow of the stream 13 into three substreams 26, 28 and 32a.

The control system 100 is used to regulate the splitting and produce the desired three separate flows, or three substreams, at the regulator 25. Sufficient methane is included in the substream 28 to create at least adequate electrical power to run the plasma reformer 15 and the auxiliary power needed for the two membrane separation operations 12 and 30. As previously, the control system 100 would monitor the amount of $CO_2$ flowing in the line 32 and supply sufficient methane in the line 32a so that the regulator/blender 33 would create the desired blend of an about 50/50 mole ratio of $CO_2$ and methane to be delivered through the line 34 to the plasma reformer 15.

When it is desired to create a substream 26 suitable for exportation to natural gas users, i.e. an export substream, it may be desirable to operate the membrane separation device 12 to produce a concentrate of methane containing a relatively small amount of $CO_2$, e.g. about 2% or less. Alternatively, the substream 26 could be subjected to a further membrane separation step and the $CO_2$ that is removed added to the stream 32. The control system 100 would, as described generally with respect to FIGS. 1 and 2, control the overall process to ultimately produce a mixture of the two feedstreams 14 and 34 that would have the desired mole ratio, e.g. about 1:1 with no more than a 2% excess of $CO_2$. Thus, from such a material gas supply, Syngas is produced as a standalone operation while also providing (1) an export methane substream of pipeline quality e.g. about 2% or less $CO_2$, and (2) excess electrical power as desired at a particular installation, i.e. above that needed to meet current requirements of the overall process.

Figure 4:
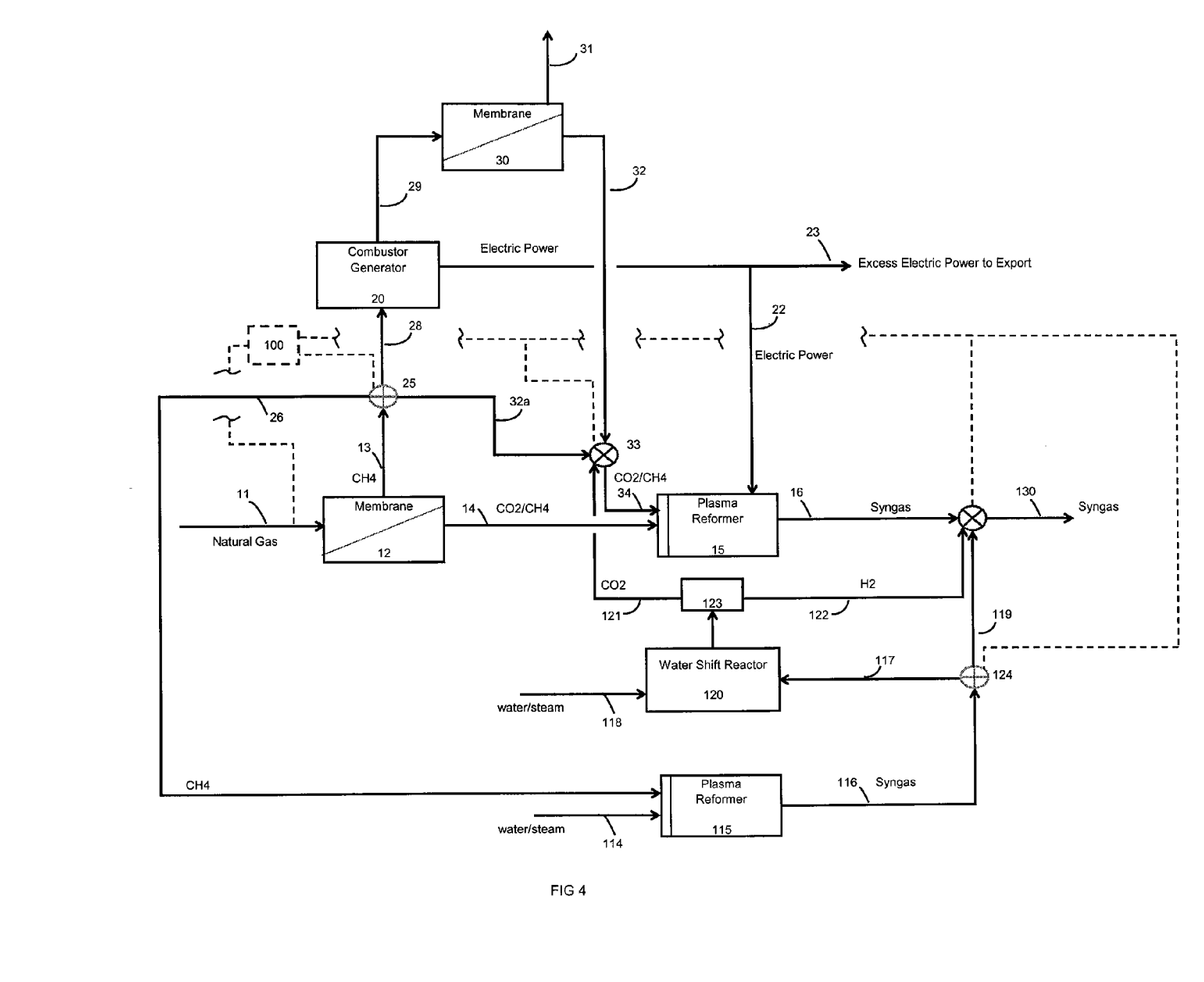
FIG. 4 is a schematic flow sheet of a system similar to FIG. 3 for processing natural gas contaminated with $CO_2$ wherein a second Syngas plasma reformer is provided that produces a second Syngas stream of higher hydrogen content which is particularly valuable for production of lower carbon chain hydrocarbons.

FIG. 4 shows a further embodiment of a process for producing Syngas from a $CO_2$-containing natural gas stream, which embodies various features of the invention and has similarity to the process illustrated in FIG. 3. Again, the incoming natural gas stream 11 would be one that contains between about 2 and about 40% carbon dioxide with the remainder being essentially methane. It is similarly delivered to a membrane separation device 12 which would separate it into a concentrate stream 13 containing predominantly methane and a permeate stream 14 that would contain carbon dioxide and methane in an about 50/50 mole ratio, for example, about 1 mole of $CO_2$ to 0.9 mole of methane. The permeate stream again serves as a first feedstream for a microwave plasma reformer 15 or the like, and the predominantly methane concentrate stream 13 is delivered to a regulator 25 which again divides the total flow of the stream 13 into three substreams 26, 28 and 32a. The substream 28, as before, is directed to a combustor/generator 20, and the substream 32a is routed to the regulator/blender 33 where it is blended with the predominantly $CO_2$ stream 32 from the membrane separation device 30 as before. However, in this installation, the substream 26 is delivered to a second plasma reformer 115 where it is mixed with a separate incoming stream of water/steam 114 that is being supplied.

The plasma reformer 115 may operate on the principles set forth in the '773 patent, and it will produce a Syngas having a higher hydrogen content than that of the plasma reformer 15 as a result of using the methane-rich stream 26 and water and/or steam. For example, the ratio of hydrogen to carbon monoxide may be about 1:1 in the Syngas produced by the plasma reformer 15, whereas by adjustment of the flows of the stream 26 and the incoming stream 114 of water and/or steam, the plasma reformer 115 may produce a ratio of as much as about 3 to 1 hydrogen to carbon monoxide in the Syngas stream 116. Furthermore, all or a portion of the Syngas stream 116, can be diverted via a flow splitter 124, to a Water Shift Reactor (WSR) 120, in which CO in the diverted portion 117 is reacted with another inflow stream of water and/or steam 118, to produce $CO_2$ and $H_2$ via the reaction $CO+H_2O \rightarrow CO_2+H_2$; this step further increases the amount of hydrogen produced. The outflow from the WSR is then separated into a $CO_2$-rich sidestream 121 and a hydrogen-rich stream 122 using, for example, a PSA (pressure swing adsorption) unit 123 as known in this art (e.g. see U.S. Pat. No. 7,740,687). The $CO_2$-rich sidestream is then fed to the regulator/blender 33 where it is combined with the methane rich stream 32a and the predominantly $CO_2$ stream 32 to form the feedstream 34 for the first plasma reformer 15. The hydrogen-rich stream 122 is combined with the Syngas streams 16 and 119, which further increases the hydrogen content in the ultimate Syngas stream 130.

EXAMPLE

An installation is operated according to the flowsheet depicted in FIG. 3 to process a natural gas source 11 containing about 10 vol % carbon dioxide and about 90 vol % methane. The natural gas is treated using the membrane separation devices and a microwave plasma reactor to produce Syngas, to produce a variable amount of pipeline quality gas for export from the methane rich product stream 13, and to produce excess electrical power for export over and above that needed to operate the overall installation. A combustor-generator 20 is used to convert some of the methane into carbon dioxide for use in the plasma reformer 15 while, at the same time, also producing the electrical power required to operate the plasma reformer. A portion of the methane rich stream 32a is fed directly to the blender/regulator 33 to match the amount of $CO_2$ being supplied from the second membrane system 30 which is producing a predominantly $CO_2$ stream 32 from the exhaust gas stream from the combustor-generator 20. In this example, the gas ratio within the composite feedstream being fed to the plasma reformer 15 is closely controlled by the control system 100 through the operation primarily of the membrane separation device 12 and the regulator 25 to produce a ratio of $CO_2/CH_4$=about 1:1 with no more than 1 or 2% excess $CO_2$.

Operation is carried out in accordance with the flowsheet depicted in FIG. 3, with an inflow stream 11 of about 1000 cubic meters per hour at standard temperature and pressure ($Nm^3/hr$) of natural gas into the membrane separation device 12. The device 12 is designed to produce a permeate stream 14 containing a suitable ratio of $CO_2/CH_4$ that will serve as a first feedstream for delivery to the plasma reformer, plus a methane rich concentrate stream 13 which contains minimal $CO_2$, preferably not greater than about 2% $CO_2$, such as is considered to be pipeline grade natural gas. A permeate stream flow is produced of about 152 $Nm^3/hr$ with a composition of about 54.5% $CO_2$ and about 45.5% $CH_4$. The methane rich stream 13 flow is about 848 $Nm^3/hr$ comprising about 98% $CH_4$ and 2% $CO_2$.

It may be desired to operate the system with no export of methane rich gas 26 from the membrane separation step 12, in order to produce excess power for export via the combustor/generator 20. The control system 100 then adjusts the flow regulator 25 so that the flow rate of methane rich stream 32a (produced from the membrane separation device 12) is sufficient to balance the predominantly $CO_2$ stream 32 coming from the second membrane separation device 30 to create a desired blend; its composition should be such that, when this feedstream 34 is combined with the permeate stream 14, a composite feedstream having the desired $CO_2/CH_4$ mole ratio, i.e. about 1:1, is created to feed the plasma reformer 15. The remainder of the methane rich stream is burned in the combustor to produce electric power which is sufficient to operate the plasma reformer 15 and the other parts of the installation, e.g. the membrane separation steps, and excess power is exported off-site. When for example about 408 Nm$^3$/hr of the methane rich stream 13 is combusted in the combustor-generator 20 to produce power, a total of about 1591 kW of power is generated by the combustor, assuming 40% efficiency in the electricity generation, which is considerably more than needed to operate the plasma reformer 15.

More particularly, the exhaust gas from the combustor-generator 20 is treated in a second membrane system 30 to produce a predominantly $CO_2$ stream 32 containing approximately 400 Nm$^3$/hr $CO_2$ (assuming about 98% recovery) which is then fed to the blender/regulator 33 where it is mixed with the stream 32$a$. As a result, the total amount of $CO_2$ in the composite feedstream delivered to the plasma reformer is about 500 Nm$^3$/hr; it is made up predominately of $CO_2$ in the permeate stream 14 plus the predominantly $CO_2$ stream 32. To provide a net $CO_2/CH_4$ mole ratio of about 1:1 in the feed to the plasma reformer, about 440 Nm$^3$/hr of the methane rich stream is sent as the stream 32$a$ to blend with the predominantly $CO_2$ stream 32, which has a flow of about 400 Nm$^3$/hr of $CO_2$. The control system 100 monitors the stream compositions and makes adjustments as needed. The total Syngas produced is about 2000 Nm$^3$/hr assuming 100% conversion, and it requires about 300 kW of power to operate the plasma reformer 15, assuming a power consumption of 0.15 kWh/m$^3$ Syngas. Thus, there is an excess power production of about 1291 kW, which can be used to operate other parts of the process plant, e.g. to power the membrane separation systems etc., and the remainder of the power can be exported off-site.

For a case where some export of pipeline quality gas is desired, about 628 Nm$^3$/hr of the methane rich substream 26 may be exported as pipeline quality gas for 1000 Nm$^3$/hr of inflow natural gas as above. In such case, only about 102 Nm$^3$/h of the methane rich stream 26 is burned in the combustor, and about 100 Nm$^3$/hr of the $CO_2$ produced is captured; this produces about 398 kW of power from the combustor-generator. The total flow of $CO_2$ in the composite feedstream being fed to the plasma reformer is only 185 Nm$^3$/hr, which is made up of the $CO_2$ in the permeate stream 14 and the predominantly $CO_2$ stream 32. To compensate for the higher percentage of $CO_2$ in the permeate stream 14, about 116 Nm$^3$/hr of methane from the methane rich stream is supplied as the stream 32$a$; this results in the desired $CO_2/CH_4$ mole ratio of about 1:1 in the composite feedstream being fed to the plasma reformer 15. The plasma reformer produces 740 Nm$^3$/hr of Syngas, and about 111 kW of power is required to operate the plasma reformer to produce this volume of Syngas, leaving excess power production of about 282 kW, assuming a combustor efficiency of 40%. This excess power can be used to operate the remainder of the installation, leaving still some power to be exported off-site.

The benefits of the process scheme depicted in FIG. 3 should be apparent, i.e. the ability to utilize the $CO_2$ impurity found in a natural gas stream and convert it to Syngas (which can then be converted to a synthetic fuel or other industrially valuable chemicals), while at the same time generating the electrical power required to operate such a plasma reformer as well as the membrane separation steps. Moreover, there is also capture of the $CO_2$ that is produced from the combustion process used to generate the electrical power.

For natural gas containing 10% $CO_2$, the process is able to utilize substantially the entire $CO_2$ content of the inflow natural gas stream, as well as that produced by burning some of the methane in order to supply all the energy required for the production of Syngas in a plasma reformer which uses methane and carbon dioxide as the only reactants. The net $CO_2$ emitted from the process is essentially zero, assuming it is all converted to Syngas in the plasma reformer, or at the very least, $CO_2$ emissions will be significantly reduced compared to conventional gas to liquid technology where all the $CO_2$ is emitted to atmosphere.

Although the invention has been described in a variety of different aspects which constitute the best modes presently known to the inventors for carrying out this invention, it should be understood that various changes and modifications as would be obvious to one having ordinary skill in this art may be made without departing from the scope of the invention, which is set forth in the claims appended hereto. For example, the incorporation of an additional plasma reformer operating on a feedstream of methane/steam/water may be included as a part of either of the FIG. 1 or FIG. 2 processes to increase the hydrogen to carbon monoxide ratio in the ultimate Syngas. An even greater increase is possible through the inclusion of a Water Shift Reactor and a PSA unit.

Particular features of the invention are emphasized in the claims that follow.

The invention claimed is:

1. A process for producing Syngas in a plasma reactor from a natural gas stream containing a significant quantity of $CO_2$, which process comprises:

providing a natural gas stream that contains $CH_4$ and between about 2 and 40% $CO_2$ and treating such stream in a semipermeable membrane device to provide a first permeate stream that contains $CO_2$ and $CH_4$ in an about 50/50 molar ratio and a methane-rich concentrate stream which is at least about 90% methane, combusting a substream from said methane-rich concentrate stream with air in a cogeneration apparatus to produce electrical power, delivering an exhaust gas stream from said cogeneration apparatus to another semipermeable membrane device and separating a predominantly $CO_2$ permeate stream, blending said predominantly $CO_2$ permeate stream with another substream of said methane-rich concentrate stream to create a blended feedstream containing $CO_2$ and $CH_4$ in an about 50/50 molar ratio, delivering a composite feedstream made up of said first permeate stream and said blended feedstream, containing $CO_2$ and $CH_4$ alone in a 1:1 mole ratio with no more than a 2% excess of $CO_2$, to a microwave plasma reactor which converts such composite feedstream to a stream of Syngas, whereby Syngas of a composition suitable as a feedstock for a Fischer-Tropsch (F-T) reactor is produced in an environmentally friendly process from natural gas containing up to about 40% $CO_2$, the overall process being controlled to generate sufficient electric power to operate said membrane separation devices and said microwave plasma reactor, and delivering said stream of Syngas as a feedstock directly to a F-T reactor which is operated to create liquid hydrocarbons, heat and tail gases.

2. The process of claim 1 wherein heat from said F-T reactor contributes to generation of electric power in the cogeneration apparatus and wherein said tail gases are combusted in the cogeneration apparatus to provide additional carbon dioxide.

3. The process of claim 1 wherein said semipermeable membrane devices employ polymeric membranes selected from the group consisting of polydimethylsilicone (PDMS), polyimides, polyarylethers, polyarylketones, polycarbonates, polysulfones, and polyacetylenes.

4. The process of claim 1 wherein said semipermeable membrane devices employ polydimethylsilicone (PDMS) sheet material as a laminate with a supporting porous polymeric membrane.

5. The process of claim 1 wherein said natural gas stream contains between about 5% and 35% $CO_2$, wherein said methane-rich concentrate stream comprises at least about 98% methane, and wherein an export substream is split from said methane-rich concentrate stream and exported as pipeline quality natural gas.

6. A process for producing Syngas in a microwave plasma reformation device from a natural gas stream containing a significant quantity of $CO_2$, which process comprises:
    providing a natural gas stream that contains $CH_4$ and between about 2 and 40% $CO_2$ and separating such stream in a semipermeable membrane device to provide a first permeate stream that is increased in $CO_2$ content and contains $CO_2$ and $CH_4$ in an about 50/50 molar ratio and a methane-rich concentrate stream containing at least about 90% methane,
    combusting a substream from said methane-rich concentrate stream with air in a cogeneration apparatus to produce electrical power,
    delivering an exhaust gas stream from the cogeneration apparatus to another semipermeable membrane device and separating a predominantly $CO_2$ permeate stream,
    blending said predominantly $CO_2$ permeate stream with another substream of said methane-rich concentrate stream to create a blended feedstream containing $CO_2$ and $CH_4$ in an about 50/50 molar ratio,
    delivering a composite feedstream made up of said first permeate stream and said blended feedstream, containing $CO_2$ and $CH_4$ alone in a 1:1 mole ratio with no more than a 2% excess of $CO_2$ to a microwave plasma reformation device which converts such to a first Syngas product stream,
    splitting a third substream from said methane-rich concentrate stream and feeding such to a second microwave plasma reformation device as a mixture with steam and/or water to convert such mixture to a second Syngas product stream of a higher hydrogen content than said first Syngas product stream, and
    combining said first and second Syngas product streams to provide an ultimate Syngas stream,
    whereby Syngas having a relatively high hydrogen content is produced in an environmentally friendly process from natural gas containing a significant quantity of $CO_2$, which process is controlled to generate sufficient electric power to operate said membrane separation devices and both said microwave plasma reformation devices.

7. The process of claim 6 wherein a portion of said second Syngas product stream, before its combining with said first Syngas product stream, is directed to a Water Shift Reactor (WSR) where a CO fraction thereof is reacted with water and/or steam to produce additional $H_2$, and wherein $H_2$ from the WSR is then combined, as a hydrogen-rich stream, with said first Syngas product stream and the remainder of said second Syngas product stream.

8. The process of claim 7 wherein the output from said WSR is delivered to a Pressure Swing Adsorption unit to produce (a) the hydrogen-rich stream and (b) a $CO_2$-rich sidestream that is added to the predominantly $CO_2$ permeate stream.

9. A process for producing Syngas in a microwave plasma reformation device from a flue gas stream and a natural gas stream, which process comprises:
    providing a flue gas stream from a carbon or hydrocarbon combustor and separating such stream in a first semipermeable membrane device into a first predominantly $CO_2$ stream and a second stream containing predominantly $N_2$,
    providing a natural gas stream that contains $CH_4$ and between about 2 and 40% $CO_2$ and separating such stream in a second semipermeable membrane device to provide a first feedstream that contains $CO_2$ and $CH_4$ in an about 50/50 molar ratio and a third stream containing at least about 90% methane,
    blending a first substream from said third stream with said first predominantly $CO_2$ stream to create a second feedstream containing $CO_2$ and $CH_4$ in an about 50/50 molar ratio,
    combusting a second substream from said third stream with air in a cogeneration apparatus to produce electrical power,
    delivering an exhaust gas stream from the cogeneration apparatus to a third semipermeable membrane device and separating a second predominantly $CO_2$ gas stream, and
    blending said second predominantly $CO_2$ stream with a third substream of said third stream to create a third feedstream containing $CO_2$ and $CH_4$ in an about 50/50 molar ratio, and
    delivering a composite feedstream made up of said first, second and third feedstreams, containing $CO_2$ and $CH_4$ alone in a 1:1 mole ratio with no more than a 2% excess of $CO_2$ to the microwave plasma reformation device which converts such to Syngas,
    whereby Syngas is produced in an environmentally friendly process from natural gas containing up to about 40% $CO_2$ and a flue gas stream, which process is controlled to generate sufficient electric power to operate said first, second and third membrane separation devices and said microwave plasma reformation device.

10. The process of claim 9 wherein said stream of Syngas is provided as a feedstock to a Fischer-Tropsch (F-T) reactor which creates liquid hydrocarbons, heat and tail gases.

11. The process of claim 10 wherein heat from said F-T reactor contributes to generation of electric power in the cogeneration apparatus and wherein said tail gases are combusted in the cogeneration apparatus to provide additional carbon dioxide in such stream.

12. The process of claim 9 wherein said second semipermeable membrane device employs a polymeric membrane selected from the group consisting of polydimethylsilicone (PDMS), polyimides, polyarylethers, polyarylketones, polycarbonates, polysulfones, and polyacetylenes.

13. The process according to claim 12 wherein said semipermeable membrane is a dimethylsilicone polymer.

14. The process of claim 9 wherein said first semipermeable membrane device employs polymeric sheet material as its semipermeable membrane and said first stream permeates through said membrane.

15. The process of claim 14 wherein said semipermeable membrane in said first semipermeable device comprises PDMS sheet material having a thickness between about 0.1 micron and 10 microns.

16. The process of claim 14 wherein said semipermeable membrane in said first semipermeable device is polydimethylsilicone sheet material as a laminate with a supporting porous polymeric membrane.

* * * * *